United States Patent
Amtmann

(10) Patent No.: US 7,915,237 B2
(45) Date of Patent: Mar. 29, 2011

(54) PRODUCTION OF PURE STEREOISOMERS OF TRICYCLO[5.2.1.0$^{2,6}$]-DEC-9-YL-XANTHOGENATE AND MEDICAMENTS THEREFROM

(75) Inventor: Eberhard Amtmann, Heidelberg (DE)

(73) Assignee: Lumavita AG, Basel (CH)

( * ) Notice: Subject to any disclaimer, the term of this patent is extended or adjusted under 35 U.S.C. 154(b) by 892 days.

(21) Appl. No.: 10/495,789

(22) PCT Filed: Nov. 2, 2002

(86) PCT No.: PCT/EP02/12242
§ 371 (c)(1),
(2), (4) Date: May 17, 2004

(87) PCT Pub. No.: WO03/041702
PCT Pub. Date: May 22, 2003

(65) Prior Publication Data
US 2005/0085448 A1    Apr. 21, 2005

(30) Foreign Application Priority Data

Nov. 17, 2001 (DE) .................. 101 56 617

(51) Int. Cl.
*A61K 31/685*    (2006.01)
*A61K 31/56*    (2006.01)
*A61K 31/21*    (2006.01)

(52) U.S. Cl. ........................ 514/78; 514/513; 514/169

(58) Field of Classification Search .............. 514/78, 514/169, 513
See application file for complete search history.

(56) References Cited

U.S. PATENT DOCUMENTS

| 4,602,037 A | * | 7/1986 | Scherm et al. | ............ 514/512 |
| 4,851,435 A | * | 7/1989 | Sauer et al. | ............ 514/512 |
| 6,756,063 B2 | * | 6/2004 | Kiss | ............ 424/630 |

FOREIGN PATENT DOCUMENTS

| JP | 57118557 | | 7/1982 |
| WO | 9614841 | | 5/1996 |
| WO | WO 96/14841 | * | 5/1996 |
| WO | WO 01/44164 | | 6/2001 |

OTHER PUBLICATIONS

Xiaoye Yang Thesis: Synthesis and use of chiral surfactants 2001 (52 pages).*
Mori et al., J. Org. Chem 4170-71.*
Sauer et al. Proc. Nat. Acad. Sci 813263-3267 (1984).*
English Translation of International Preliminary Examination Report for International Patent Application No. PCT/EP2002/012242 dated Jul. 15, 2004.
Albert González-Roura, et al. "Synthesis and Phospholipase C Inhibitory Activity of D609 Diastereomers", *Lipids* 37, (4), 401-406, (2002).
Sauer, et al., "DNA and RNA Virus Species are Inhibited by Xanthanes, a Class of Antiviral Compounds with Unique Properties", Proc. Natl. Acad. Sci, USA, vol. 81, (Jun. 1984), p. 3263-3267.

* cited by examiner

*Primary Examiner* — Brandon J Fetterolf
*Assistant Examiner* — Shirley V Gembeh
(74) *Attorney, Agent, or Firm* — Drinker Biddle & Reath LLP

(57) ABSTRACT

The invention relates to pharmaceutical formulations containing exo/exo-tricyclo[5.2.1.0$^{2,6}$]-dec-9-yl-xanthogenate, drugs containing exo/exo-tricyclo[5.2.1.0$^{2,6}$]-dec-9-yl-xanthogenate as active ingredient for the treatment of genital herpes, labial herpes, AIDS, tumors or autoimmune diseases, and methods for the production of pure stereoisomers of tricyclo[5.2.1.0$^{2,6}$]-decan-9-ol and tricyclo[5.2.1.0$^{2,6}$]-dec-9-yl-xanthogenate.

19 Claims, 3 Drawing Sheets

○ Exo/Exo-tricyclo[5.2.1.0$^{2.6}$]-dec-9-yl-xanthogenate
□ Mixture of isomers of tricyclo[5.2.1.0$^{2.6}$]-dec-9-yl-xanthogenate

PRODUCTION OF PURE STEREOISOMERS OF TRICYCLO[5.2.1.0$^{2.6}$]-DEC-9-YL-XANTHOGENATE AND MEDICAMENTS THEREFROM

The present invention relates to pharmaceutical formulations containing exo/exo-tricyclo[5.2.1.0$^{2.6}$]-dec-9-yl-xanthogenate, drugs containing exo/exo-tricyclo[5.2.1.0$^{2.6}$]-dec-9-yl-xanthogenate as active ingredient for the treatment of genital herpes, labial herpes, AIDS, tumors or autoimmune diseases, and methods for the production of pure stereoisomers of tricyclo[5.2.1.0$^{2.6}$]-decan-9-ol and tricyclo [5.2.1.0$^{2.6}$]-dec-9-yl-xanthogenate.

The battle against viral diseases is a considerable challenge since viruses make use of the body's inherent mechanisms for their proliferation. Moreover, by means of rapid mutation viruses can render initially efficacious therapeutic agents ineffective after very short times. Consequently, there is a constant need for new and more efficacious drugs against viral diseases.

Printed patent specification, U.S. Pat. No. 4,602,037, describes xanthogen derivatives corresponding to general formula I:

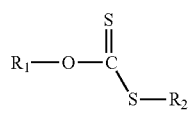

whereby R$_1$ corresponds to a possibly substituted aryl or alkyl residue, as well as the use thereof as antiviral agents. Cyclododecyl, dodecyl, benzyl, cyclohexyl, adamantyl, tricyclo[5,2,1,0$^{2.6}$]-decyl, 4-isobornylcyclohexyl, and bicyclo [2,2,1$^{1.4}$]-heptyl are disclosed as examples of R$_1$.

U.S. Pat. No. 4,981,869 describes the same compounds as U.S. Pat. No. 4,602,037 for use as antitumor agents.

U.S. Pat. No. 4,851,435 describes the use of ionic detergents as effect-enhancing adjuvants for xanthogen derivatives corresponding to formula I.

WO 96/14841 discloses the incorporation of xanthogenates corresponding to formula I and of adjuvants into lipid- or steroid-based carrier substances. The incorporation into a carrier substance is designed to improve the tolerability of the agents.

DE 101 17 728, which had not been the subject of prior publication, discloses pharmaceutical formulations containing a xanthogenate, optionally an activity-enhancing adjuvant, and an emulsifying agent that reduces the irritant effect of xanthogenate and activity-enhancing adjuvant. With regard to its substance, the emulsifying agent corresponds to the carrier substance named in WO 96/14841. However, in contrast to WO 96/14841, active ingredient and emulsifying agent are only being mixed according to DE 101 17 728. The incorporation of the active ingredient into the carrier is dispensable which simplifies the method considerably.

In all of these publications, tricyclo[5.2.1.0$^{2.6}$]dec-9-yl-xanthogenate is included amongst the preferred compounds. Tricyclo[5.2.1.0$^{2.6}$]dec-9-yl-xanthogenate can be present in the form of four different isomers: exo/exo, exo/endo, endo/exo, and endo/endo. The publications cited above concerned mixtures of isomers that were not defined to any detail. Printed patent specification U.S. Pat. No. 4,602,037 describes both exo- and endo isomers of bicyclo[2,2,1$^{1.4}$]-heptyl xanthogenate and their antiviral effect is being reported to be identical.

It was now surprisingly found that isomerically pure tricyclo[5.2.1.0$^{2.6}$]dec-9-yl-xanthogenate possesses considerably improved antiviral efficacy as compared to the mixture of isomers described according to the state-of-the-art. The pure exo/exo isomer shows approx. 4-10-fold stronger antiviral effect than the mixture containing 83% exo/exo isomer and 17% of the exo/endo, endo/exo, and endo/endo isomers. This mixture is obtained upon conversion of commercially available tricyclo[5.2.1.0$^{2.6}$]decan-9-ol with alkali metal and CS$_2$ in inert solvents.

Figure 1:
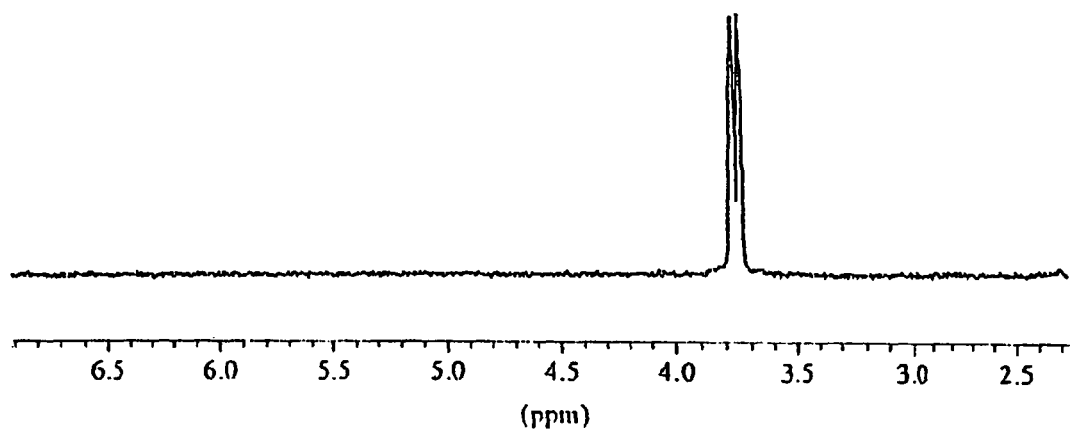
FIG. 1 depicts a part of the $^1$H-NMR spectrum of the first fraction obtained upon fractional distillation of a commercially available mixture of tricyclo[5.2.1.0$^{2.6}$]decan-9-ol isomers at 10$^4$ torr and 49° C.

Therefore, the present invention relates to pharmaceutical formulations and drugs made therefrom containing pure exo/exo-tricyclo[5.2.1.0$^{2.6}$]dec-9-yl-xanthogenate as active ingredient. The drugs according to the invention are suitable for the treatment of viral, tumor, and autoimmune diseases. The term "pure isomer" as used hereinafter shall refer to compounds containing in addition to the named isomer no more than 5%, preferably no more than 1% and in particular less than 0.1%, of the other possible isomers.

It was surprisingly found that the exo/exo, exo/endo, endo/exo, and endo/endo isomers of tricyclo[5.2.1.0$^{2.6}$]decan-9-ol can be separated by fractional distillation and the pure isomers are maintained during conversion to the xanthogenates.

Therefore, the invention also relates to the production of pure isomers of tricyclo[5.2.1.0$^{2.6}$]decan-9-ol and tricyclo [5.2.1.0$^{2.6}$]dec-9-yl-xanthogenate.

In addition to the active ingredient, the drugs according to the invention can also contain common carrier substances and excipients. Other active ingredients can be contained therein as well provided they do not adversely affect the effect or the stability of the xanthogenate according to the invention.

In particular, the adjuvants known from U.S. Pat. No. 4,851,435, preferably ionic detergents, and particularly preferably a fatty acid with 6-19 carbon atoms or the salt thereof, are added. The potassium salts of decanoic, undecanoic or lauric acid are particularly preferred. The activity-enhancing adjuvant can also be a sulfate with an aliphatic residue of 8-18 carbon atoms. Sodium lauric acid sulfate is particularly preferred. Moreover, the adjuvant can be deoxycholic acid or a pharmaceutically tolerable salt thereof or a phosphonic acid.

Moreover, active ingredient and adjuvant, if any, can be incorporated into lipid- or steroid-based carrier substances according to WO 96/14841, in particular into a steroid such as cholesterol, cholestanol, cholanic acid, chondrillasterol, and α, β, γ sisterol. In particular, active ingredient and adjuvant, if any, are mixed with the carrier substance according to DE 101 17 728. Cholesterol is particularly preferred. Phospholipids are also suitable carrier substances, in particular phosphatidylcholine, phosphafidylserine, phosphatidylinositol or stearylamine.

Particularly preferred is a formulation containing exo/exo-tricyclo[5.2.1.0$^{2.6}$]dec-9-yl-xanthogenate and the Na or K salt of decanoic acid as the activity-enhancing adjuvant, and cholesterol. In particular, one part xanthogenate is used with one part potassium salt of decanoic acid and 4 parts cholesterol.

Another preferred formulation contains exo/exo-tricyclo[5.2.1.0$^{2.6}$]dec-9-yl-xanthogenate, phosphatidylcholine, and the Na or K salt of decanoic acid as the activity-enhancing adjuvant. In particular, one part xanthogenate is used with one part decanoic acid and 4 parts phosphatidylcholine.

The drugs according to the invention can be formulated in the form of oral, parenteral, and topical forms of administration, and as solutions for injection. Topical application in the form of ointments is preferred whereby a lipophilic substance is used as the ointment base. Preferably, Vaseline is used as the ointment base.

The dosage depends on the severity and course of the disease, whereby the higher efficacy of the isomerically pure xanthogenate according to the invention allows the dose to be reduced as compared to the administration of the mixture of isomers. Typically, ointments containing concentrations of 0.5 to 10%, in particular 1 to 5%, xanthogenate are applied several times daily to the skin area to be treated.

The following examples further illustrate the invention, though without restricting the scope of the invention.

EXAMPLE 1

Production of Exo/exo-tricyclo[5.2.1.0$^{2.6}$]decan-9-ol

Figure 2:
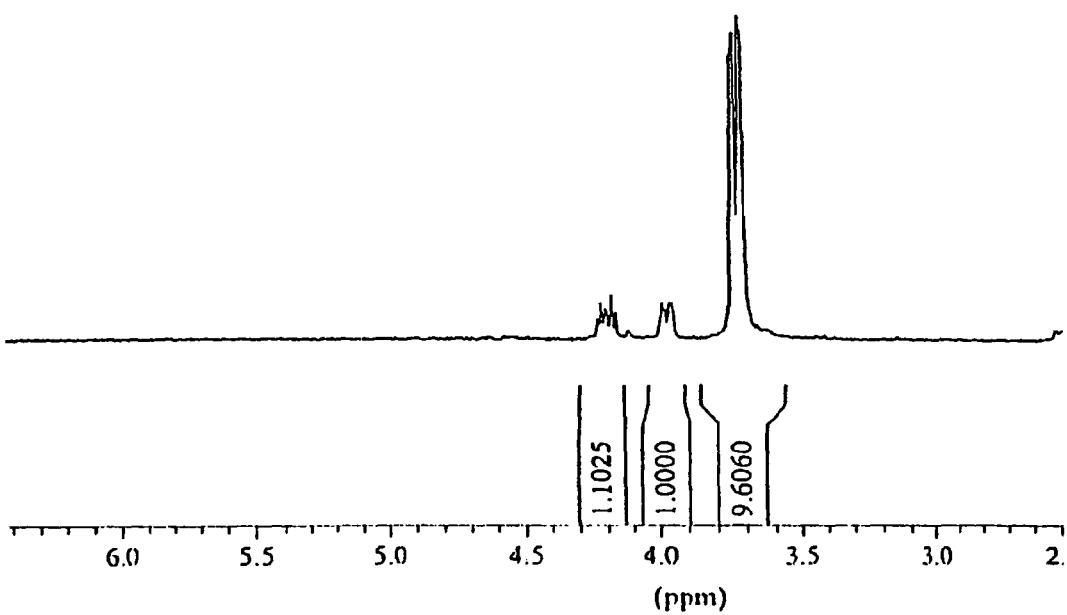
FIG. 2 depicts the NMR spectrum of a mixture of tricyclo [5.2.1.0$^{2.6}$]decan-9-ol isomers.

A commercially available mixture of tricyclo[5.2.1.0$^{2.6}$]decan-9-ol isomers was distilled in a vacuum (10$^{-4}$ torr) at 49° C. The first fraction collected was the pure exo/exo isomer. The isomers can be identified in the NMR spectrum. FIG. 1 shows a part of the $^1$H-NMR spectrum of the first fraction. The spectrum was recorded in CDCl$_3$ solution with a Bruker DRX 250 spectrometer at 250 MHz using CHCl$_3$ as the standard. It is evident that the exo/exo isomer shows a double peak between 3.7 and 3.8 ppm. FIG. 2 shows the corresponding spectrum of the mixture of isomers. The other isomers show peaks at approx. 4.0 ppm and between 4.1 and 4.3 ppm.

EXAMPLE 2

Production of Exo/exo-tricyclo[5.2.1.0$^{2.6}$]dec-9-yl-xanthogenate

A total of 457 g (approx. 3 mol) exo/exo-tricyclo[5.2.1.0$^{2.6}$]decan-9-ol, added in several aliquots, were mixed with a total of 19.55 g potassium (after removal of the surface crust) by stirring at 150 to 160° C. in a protective gas atmosphere (nitrogen). The mixture was maintained at this temperature until all metal was converted. Subsequently, the excess of the alcohol was removed by distillation in a vacuum. The alcoholate was dried in a vacuum and then dissolved in 500 ml tetrahydrofuran. Under cooling, 31 ml (0.5 mol) CS$_2$ in 150 ml ether were added in the form of separate aliquots. The mixture was stirred for 1 h at 40° C. The xanthogenate was precipitated by adding 1 l anhydrous ether, collected by suction filtration, and thoroughly rinsed with ether on the filter. After recrystallization from ethanol, 104 g (78% of theoretical yield) fine yellow needles were obtained. The purity was demonstrated by NMR spectroscopy.

EXAMPLE 3

Figure 3:
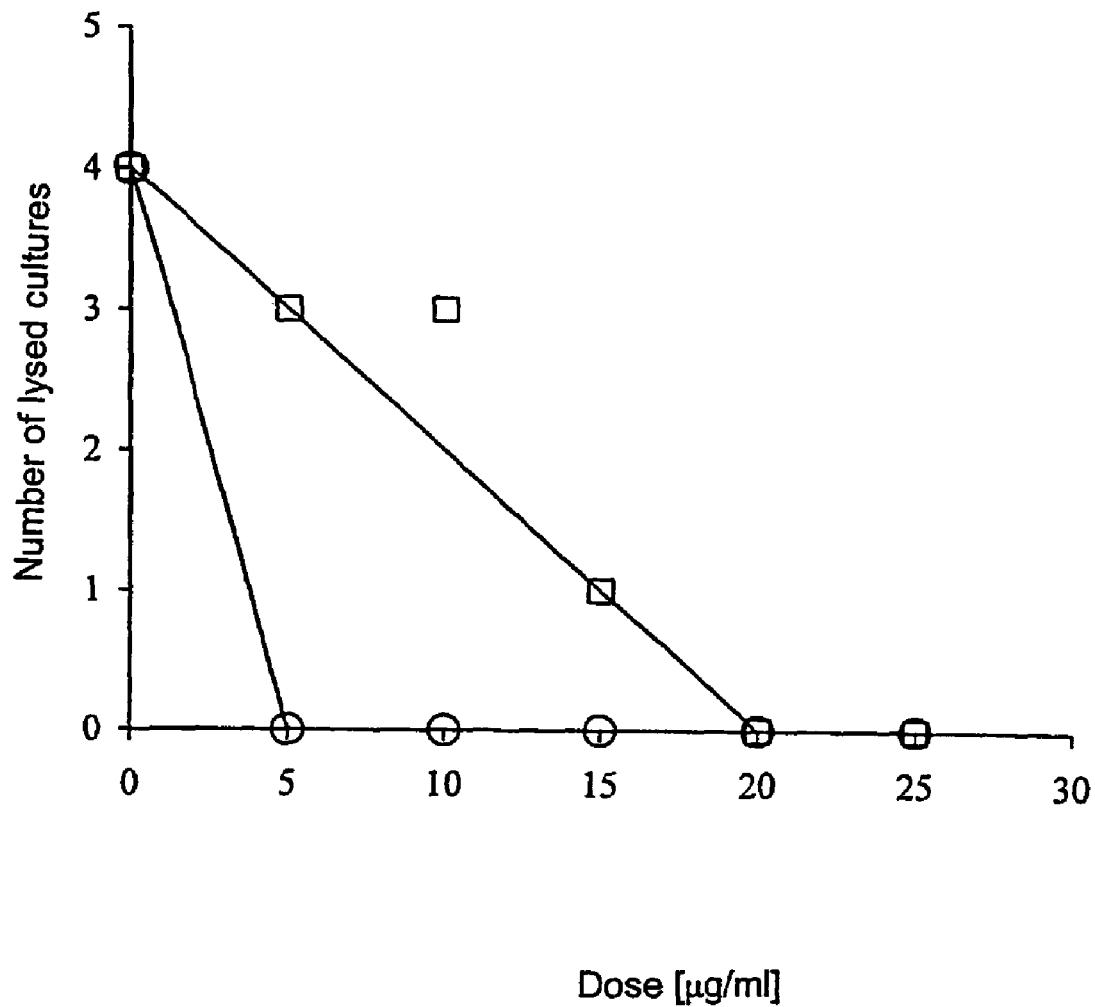
FIG. 3 is a graph showing the inhibition of the proliferation of Herpes via the cytopathogenic effect using exo/exo-tricyclo[5.2.1.0$^{2.6}$]dec-9-yl-xanthogenate and a mixture of xanthogenate isomers.

The inhibition of the proliferation of Herpes by exo/exo-tricyclo[5.2.1.0$^{2.6}$]dec-9-yl-xanthogenate was determined by measuring the cytopathogenic effect. For this purpose, monkey kidneys cells (Rita strain) were seeded on Linbro plates. After 24 hours, 50 plaque-forming units of Herpes simplex virus 1 were added to each culture. After allowing for adsorption for one hour, fresh culture medium adjusted to pH 6.8 was added. Four cultures each were treated either with the pure exo/exo isomer or a mixture of isomers containing 83% of the exo/exo isomer using the following concentrations: 0, 5, 10, 15 or 20 µg/ml. The cultures were analyzed by microscopy after 6 days. The results are shown in FIG. 3. Untreated cultures were completely lysed as a result of virus proliferation (cytopathogenic effect). All cultures treated with the exo/exo isomer showed no evidence of a cytopathogenic effect. This means that proliferation of the virus was completely suppressed even at the concentration of 5 µg/ml. The mixture of isomers showed this effect only at a concentration of 20 µg/ml.

EXAMPLE 4

Figure 4:
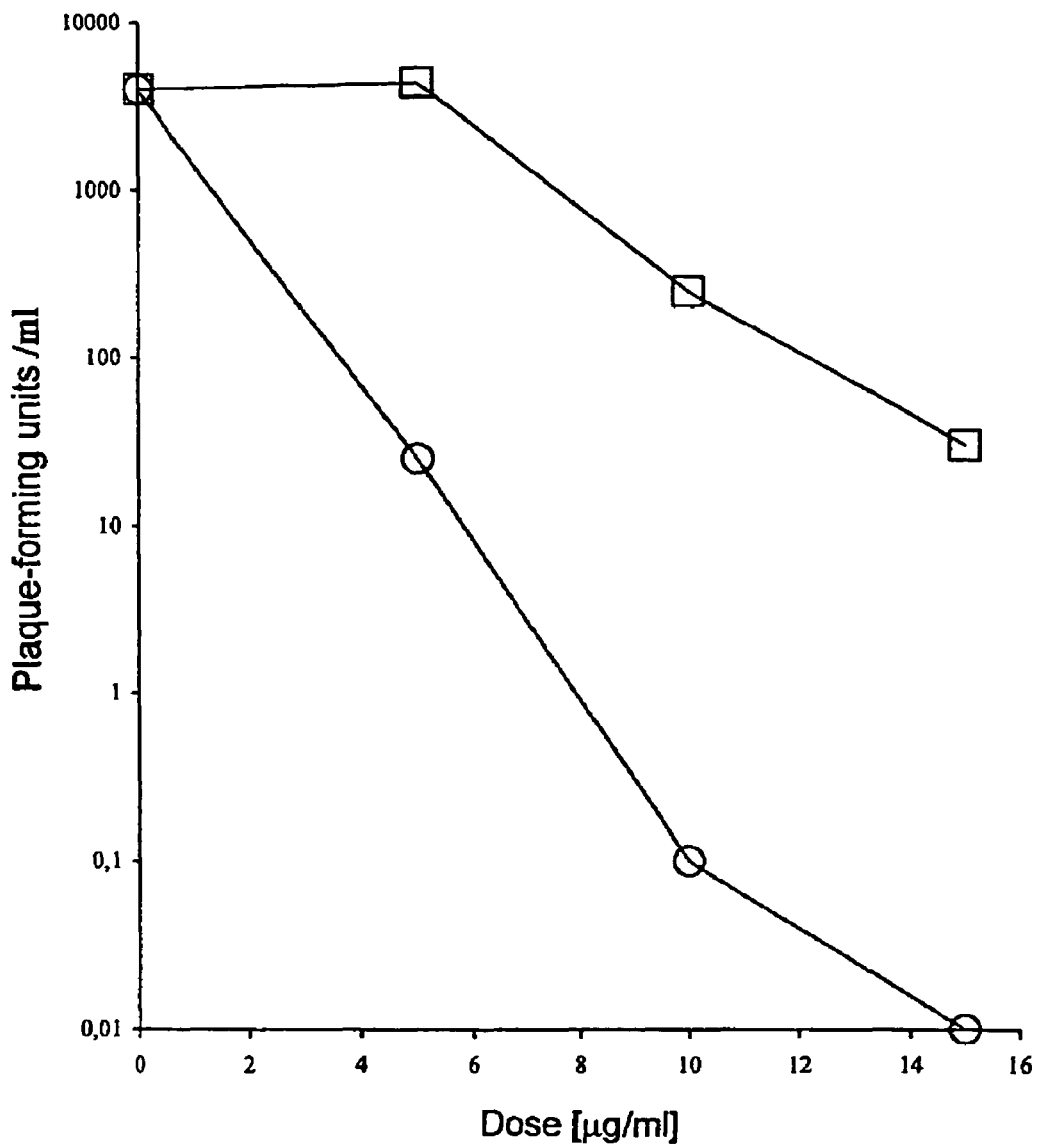
FIG. 4 is a graph of the dose response curves for exo/exo-tricyclo[5.2.1.0$^{2.6}$]dec-9-yl-xanthogenate and a mixture of xanthogenate isomers for the inhibition of Herpes virus proliferation.

The inhibition of the proliferation of Herpes by exo/exot-ricyclo[5.2.1.0$^{2.6}$]dec-9-yl-xanthogenate was determined by measuring viral proliferation. For this purpose, monkey kidneys cells (Rita strain) were seeded on Linbro plates. After 24 hours, 100 plaque-forming units of Herpes simplex virus 1 were added to each culture. After allowing for adsorption for one hour, fresh culture medium adjusted to pH 6.8 was added. Four cultures each were treated either with the pure exo/exo isomer or a mixture of isomers containing 83% of the exo/exo isomer using the following concentrations: 0, 5, 10 or 15 µg/ml. The virus concentrations in the supernatants of the cultures were determined after four days by means of plaque assays. The means for each concentration were calculated and entered in a dose-response curve as shown in FIG. 4. The curves were used to determine the concentration at which viral proliferation was inhibited by 50% (IC50). An IC50 of 0.6 µg/ml was found for the exo/exo isomer. The IC50 of the mixture of isomers was found to be 7.6. This means that the pure exo/exo isomer effected a 50% reduction of viral proliferation at a more than 10-fold lower concentration as compared to the mixture of isomers.

The invention claimed is:

1. A pharmaceutical formulation comprising a xanthogenate corresponding to formula I

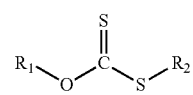

wherein
R$_1$ corresponds to tricyclo[5.2.1.0$^{2.6}$]-dec-9-yl,
R$_2$ corresponds to a metal atom, ammonium, or substituted or unsubstituted alkyl;
and at least 95% of said xanthogenate in said formulation is exo/exo-tricyclo[5.2.1.0$^{2.6}$]-dec-9-yl xanthogenate and no more than 5% of said xanthogenate in said formulation is any other possible isomer of said xanthogenate.

2. The pharmaceutical formulation according to claim 1, wherein R$_2$ is a sodium atom, a potassium atom, dimethylglycyl, or methyl.

3. The pharmaceutical formulation according to claim 1, further comprising a steroid or a phospholipid to reduce the irritant effect of the xanthogenate.

4. The pharmaceutical formulation according to claim 3, wherein the steroid or phospholipid is selected from the group consisting of cholesterol and phosphatidylcholine.

5. The pharmaceutical formulation according to claim 3, comprising 1-10 parts steroid or phospholipid per one part xanthogenate.

6. The pharmaceutical formulation according to claim 3, comprising 2 to 4 parts steroid or phospholipid per one part xanthogenate.

7. The pharmaceutical formulation according to claim 1, further comprising an ionic detergent as an adjuvant to enhance the activity of the xanthogenate.

8. The pharmaceutical formulation according to claim 7, wherein the ionic detergent is a fatty acid with 6 to 19 carbon atoms or an alkyl sulfate with 8 to 18 carbon atoms.

9. The pharmaceutical formulation according to claim 1, further comprising deoxycholic acid or a pharmaceutically tolerable salt thereof as an adjuvant to enhance the activity of the xanthogenate.

10. The pharmaceutical formulation according to claim 1, further comprising a phosphonic acid as an adjuvant to enhance the activity of the xanthogenate.

11. The pharmaceutical formulation according to claim 1, wherein the formulation is an ointment or cream.

12. A method for the treatment of genital herpes, labial herpes, or AIDS, comprising administering the pharmaceutical formulation of claim 1 to a patient in need thereof.

13. The pharmaceutical formulation according to claim 1, wherein $R_2$ is a sodium or potassium atom.

14. A method for the production of an isomer of tricyclo[5.2.1.0$^{2.6}$]decan-9-ol, comprising subjecting a mixture of tricyclo[5.2.1.0$^{2.6}$]decan-9-ol stereoisomers to fractional distillation under reduced pressure and collecting a distillate, wherein said collected distillate contains at least 95% of a single isomer of tricyclo[5.2.1.0$^{2.6}$]decan-9-ol and no more than 5% of any other isomer of tricyclo[5.2.1.0$^{2.6}$]decan-9-ol.

15. The method of claim 14, wherein said single isomer is exo/exo tricyclo[5.2.1.0$^{2.6}$]decan-9-ol.

16. A method for the production of an isomer of tricyclo[5.2.1.0$^{2.6}$]dec-9-yl-xanthogenate, comprising the steps of:
    reacting a composition containing at least 95% of a single isomer of tricyclo[5.2.1.0$^{2.6}$]decan-9-ol and no more than 5% of any other isomer of tricyclo[5.2.1.0$^{2.6}$]decan-9-ol with an alkali metal or metal hydride to generate an alcoholate,
    dissolving the alcoholate in an inert solvent, and
    adding $CS_2$ to the alcoholate to form an isomer of tricyclo[5.2.1.0$^{2.6}$]dec-9-yl-xanthogenate having at least 95% of a single isomer of tricyclo[5.2.1.0$^{2.6}$]dec-9-yl-xanthogenate and no more than 5% of any other isomer of tricyclo[5.2.1.0$^{2.6}$]dec-9-yl-xanthogenate.

17. A composition comprising a compound according to formula I

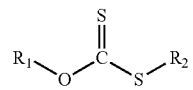

I wherein
  $R_1$ corresponds to tricyclo[5.2.1.0$^{2.6}$]-dec-9-yl,
  $R_2$ corresponds to a metal atom, ammonium, or substituted or unsubstituted alkyl;
and at least 95% of said compound according to formula I in said composition is exo/exo-tricyclo[5.2.1.0$^{2.6}$]-dec-9-yl xanthogenate and no more than 5% of said compound in said composition is any other possible isomer of said xanthogenate.

18. The composition of claim 17, wherein $R_2$ is a sodium atom, a potassium atom, dimethylglycyl, or methyl.

19. The composition of claim 17, wherein $R_2$ is a sodium or potassium atom.

* * * * *